(12) United States Patent
Schmidt

(10) Patent No.: US 9,636,518 B2
(45) Date of Patent: May 2, 2017

(54) NESTED DOUBLE HELIX CONDUCTORS

(71) Applicant: Medical Energetics Ltd., Galway (IE)

(72) Inventor: David G. Schmidt, Poway, CA (US)

(73) Assignee: Medical Energetics Ltd., Galway (IE)

( * ) Notice: Subject to any disclaimer, the term of this patent is extended or adjusted under 35 U.S.C. 154(b) by 332 days.

(21) Appl. No.: 14/506,451

(22) Filed: Oct. 3, 2014

(65) Prior Publication Data

US 2015/0119632 A1    Apr. 30, 2015

Related U.S. Application Data

(60) Provisional application No. 61/962,014, filed on Oct. 28, 2013.

(51) Int. Cl.
| | | |
|---|---|---|
| *A61N 2/02* | (2006.01) | |
| *H03G 3/00* | (2006.01) | |
| *H01F 27/00* | (2006.01) | |
| *H01F 5/00* | (2006.01) | |
| *H01F 27/28* | (2006.01) | |
| *A61N 1/40* | (2006.01) | |

(52) U.S. Cl.
CPC ............. *A61N 2/02* (2013.01); *H01F 5/00* (2013.01); *A61N 1/40* (2013.01); *Y10T 307/305* (2015.04)

(58) Field of Classification Search
CPC ........ A61N 2/02; A61N 1/40; Y10T 307/305; H01F 5/00
See application file for complete search history.

(56) References Cited

U.S. PATENT DOCUMENTS

| | | |
|---|---|---|
| 1,898,661 A | 2/1933 | Hagen |
| 2,035,274 A | 3/1936 | Mougey |
| 2,297,454 A | 9/1942 | Berger |
| 2,850,666 A | 9/1958 | Brewer |
| 3,037,175 A | 5/1962 | Ruthroff |
| 3,066,295 A | 11/1962 | Krause |
| 3,519,964 A | 7/1970 | Chorney |
| 3,588,689 A | 6/1971 | Crawford |
| 3,683,393 A | 8/1972 | Self |
| 3,760,812 A | 9/1973 | Timm et al. |
| 3,774,452 A | 11/1973 | Tullos et al. |
| 4,131,759 A | 12/1978 | Felkel |
| 4,229,676 A | 10/1980 | Manoly |
| 4,266,532 A | 5/1981 | Ryaby et al. |
| 4,439,702 A | 3/1984 | Belikov et al. |
| 4,489,276 A | 12/1984 | Yu |
| 4,832,051 A | 5/1989 | Jarvik et al. |
| 4,989,617 A | 2/1991 | Memberg |
| 5,077,934 A | 1/1992 | Liboff et al. |
| 5,079,458 A | 1/1992 | Schuster |
| 5,173,669 A | 12/1992 | Manoly |

(Continued)

FOREIGN PATENT DOCUMENTS

| | | |
|---|---|---|
| GB | 479841 A | 2/1938 |
| GB | 2480610 A | 11/2011 |

(Continued)

*Primary Examiner* — Christine H Matthews
*Assistant Examiner* — Joshua D Lannu
(74) *Attorney, Agent, or Firm* — Sheppard Mullin Richter & Hampton LLP

(57) ABSTRACT

An electrical system including multiple bodies having an underlying structure resembling a double helix may be used to produce useful electromagnetic fields for various applications.

34 Claims, 14 Drawing Sheets

(56) References Cited

U.S. PATENT DOCUMENTS

| | | |
|---|---|---|
| 5,182,537 A | 1/1993 | Thuis |
| 5,339,061 A | 8/1994 | Reick |
| 5,359,340 A | 10/1994 | Yokota |
| 5,366,493 A | 11/1994 | Scheiner et al. |
| 5,464,456 A | 11/1995 | Kertz |
| 5,654,723 A | 8/1997 | Craven et al. |
| 5,819,467 A | 10/1998 | Zucker |
| 5,851,206 A | 12/1998 | Guglielmi |
| 5,892,480 A | 4/1999 | Killen |
| 5,909,165 A | 6/1999 | Leupold |
| 5,954,630 A | 9/1999 | Masaki et al. |
| 5,977,932 A | 11/1999 | Robinson |
| 6,005,462 A | 12/1999 | Myers |
| 6,169,523 B1 | 1/2001 | Ploussios |
| 6,239,760 B1 | 5/2001 | Van Voorhies |
| 6,300,920 B1 | 10/2001 | Pertl et al. |
| 6,520,986 B2 | 2/2003 | Martin |
| 6,552,530 B1 | 4/2003 | Vaiser et al. |
| 6,770,023 B2 | 8/2004 | Vaiser et al. |
| 6,921,042 B1 | 7/2005 | Goodzeit et al. |
| 6,978,179 B1 | 12/2005 | Flagg et al. |
| 7,148,783 B2 | 12/2006 | Parsche et al. |
| 7,154,368 B2 | 12/2006 | Sweeney et al. |
| 7,375,449 B2 | 5/2008 | Butterfield |
| 8,323,328 B2 | 12/2012 | Martin |
| 8,463,407 B2 | 6/2013 | Bulkes et al. |
| 8,652,023 B2 | 2/2014 | Schmidt |
| 8,653,925 B2 | 2/2014 | Schmidt |
| 8,749,333 B2 | 6/2014 | Schmidt |
| 8,919,035 B2 | 12/2014 | Schmidt |
| 8,961,384 B2 | 2/2015 | Schmidt |
| 9,030,283 B2 | 5/2015 | Schmidt |
| 9,370,667 B2 | 6/2016 | Schmidt |
| 9,406,421 B2 | 8/2016 | Schmidt |
| 9,504,845 B2 | 11/2016 | Schmidt |
| 2003/0011527 A1 | 1/2003 | Kokorin |
| 2003/0158585 A1 | 8/2003 | Burnett |
| 2003/0169132 A1 | 9/2003 | Vaiser et al. |
| 2003/0230427 A1 | 12/2003 | Gareis |
| 2005/0094989 A1 | 5/2005 | Halpin |
| 2005/0121396 A1 | 6/2005 | Kosakewich |
| 2007/0024520 A1 | 2/2007 | Preble |
| 2007/0258329 A1 | 11/2007 | Winey |
| 2008/0161884 A1 | 7/2008 | Chandler et al. |
| 2008/0266203 A1 | 10/2008 | Rossetto et al. |
| 2009/0083969 A1 | 4/2009 | Meinke |
| 2009/0206974 A1 | 8/2009 | Meinke |
| 2009/0260849 A1 | 10/2009 | Cardas |
| 2010/0005711 A1 | 1/2010 | Mcneff |
| 2010/0057655 A1 | 3/2010 | Jacobson et al. |
| 2010/0113862 A1 | 5/2010 | Kotowich et al. |
| 2010/0114280 A1 | 5/2010 | Hill |
| 2010/0152811 A1 | 6/2010 | Flaherty |
| 2010/0179630 A1 | 7/2010 | Williams |
| 2012/0101366 A1 | 4/2012 | Ruohonen et al. |
| 2012/0143285 A1 | 6/2012 | Wang et al. |
| 2012/0223800 A1* | 9/2012 | Schmidt ............... H05H 7/04 336/229 |
| 2013/0192129 A1 | 8/2013 | Schmidt |
| 2013/0211181 A1 | 8/2013 | Schmidt |
| 2013/0285782 A1 | 10/2013 | Schmidt |
| 2014/0097925 A1 | 4/2014 | Schmidt |
| 2014/0100412 A1 | 4/2014 | Schmidt |
| 2014/0218149 A1 | 8/2014 | Schmidt |
| 2014/0371514 A1 | 12/2014 | Schmidt |
| 2015/0119630 A1 | 4/2015 | Schmidt |
| 2015/0119631 A1 | 4/2015 | Schmidt |
| 2015/0157871 A1 | 6/2015 | Schmidt |
| 2015/0283393 A1 | 10/2015 | Schmidt |
| 2015/0283394 A1 | 10/2015 | Schmidt |
| 2016/0172088 A1 | 6/2016 | Schmidt |
| 2016/0172101 A1 | 6/2016 | Schmidt |
| 2016/0247614 A1 | 8/2016 | Schmidt et al. |
| 2016/0247617 A1 | 8/2016 | Schmidt et al. |
| 2016/0365186 A1 | 12/2016 | Schmidt |

FOREIGN PATENT DOCUMENTS

| | | |
|---|---|---|
| WO | 2012118971 A2 | 9/2012 |
| WO | 2013112810 A1 | 8/2013 |
| WO | 2013123009 A1 | 8/2013 |

* cited by examiner

NESTED DOUBLE HELIX CONDUCTORS

RELATED APPLICATIONS

This application is related to U.S. Pat. No. 8,653,925, entitled "Double Helix Conductor," which issued Feb. 18, 2014. This application is related to U.S. patent application Ser. No. 14/194,412, entitled "Health Applications for Using Bio-Feedback to Control an Electromagnetic Field," which was filed Feb. 28, 2014. The related patent(s) and application(s) are hereby incorporated by reference into the present application in their entirety.

FIELD OF THE INVENTION

The invention relates to combinations of multiple bodies structured as helically wound runners around which one or more conductive wires may be wound, electrical devices and/or systems configured to include multiple bodies, the manufacture thereof and/or electrical devices and/or systems including multiple bodies. The invention relates to methods of operation of these devices and systems, and applications thereof. The invention relates to electrical devices and/or systems configured to provide therapy to patients by using electromagnetic fields.

BACKGROUND OF THE INVENTION

It is known that spirally wound electrical conductors may exhibit certain electromagnetic properties and/or generate particular electromagnetic fields and/or waves. For example, it is known that an electromagnetic coil may act as an inductor and/or part of a transformer, and has many established useful applications in electrical circuits. One or more electromagnetic coils may be used to exploit the electromagnetic field and/or wave that is created when, e.g., one or more active current sources are operatively coupled to the one or more coils.

SUMMARY

One aspect of the invention relates to an electrical system comprising multiple bodies and conductive wires. Individual bodies may include two intertwined helically wound runners. A first runner is coupled to the second runner by struts. Individual bodies may be arranged in toroidal shapes. Individual bodies may have different sizes such that a smaller body may be arranged within a larger body. Bodies may be arranged so that a smaller body and a larger body are nested. The conductive wires may be spirally wound around at least one runner of an individual body.

These and other objects, features, and characteristics of the present disclosure, as well as the methods of operation and functions of the related components of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the any limits. As used in the specification and in the claims, the singular form of "a", "an", and "the" include plural referents unless the context clearly dictates otherwise.

DETAILED DESCRIPTION

Figure 1:
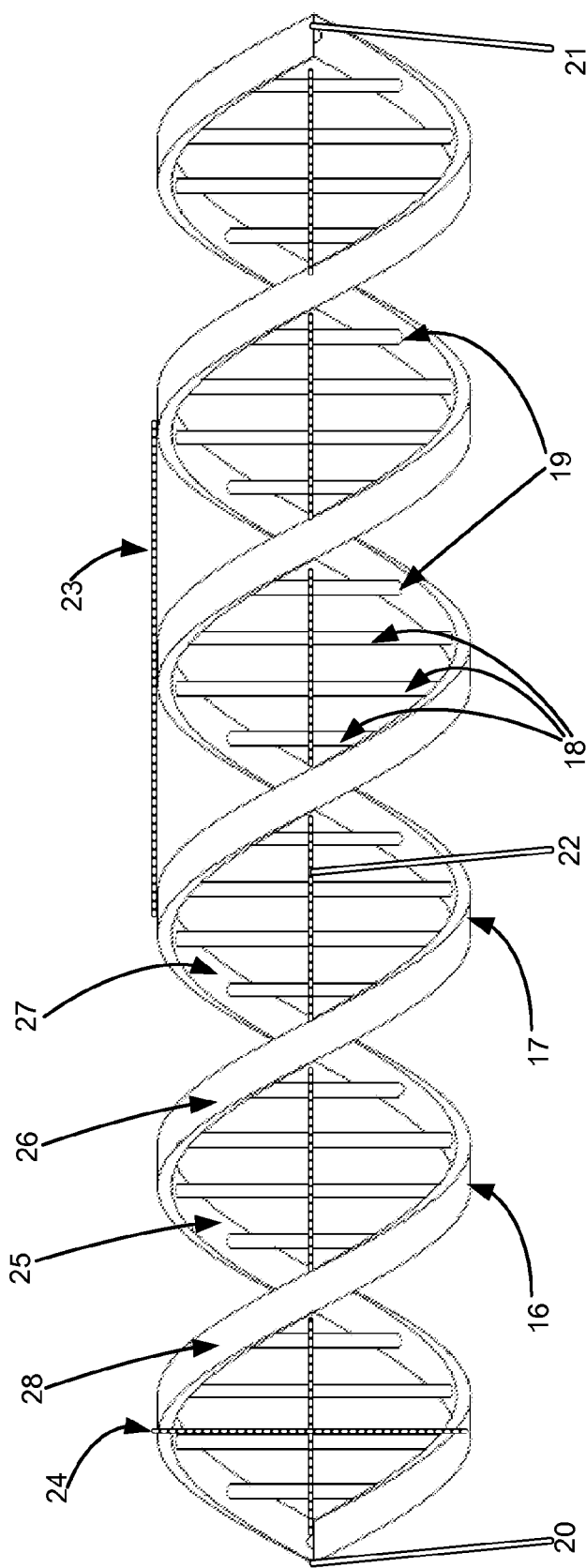
FIG. 1 illustrates a side view of an exemplary body including two intertwined helically wound runners, coupled by struts.

FIG. 1 illustrates a side view of an exemplary body 15. Body 15 may include two or more intertwined helically wound runners—runner 16 and runner 17. Runner 16 and runner 17 may be coupled by struts 18. Body 15 includes two ends—end 20 and end 21—disposed at opposite sides of body 15. Runners 16 and/or 17 may be arranged in the shape of a three-dimensional curve similar to or substantially the same as a helix. A helix may be characterized by the fact that a tangent line at any point along the curve has a constant angle with a (fixed) line called the axis. The pitch of a helix may be the width of one 360 degree helix turn (a.k.a. revolution), e.g. measured parallel to the axis of the helix. Intertwined helically wound runners may share the same axis, be congruent, and/or differ by a translation along the axis, e.g. measuring half the pitch. The two runners shown in FIG. 1 may share the same axis 22, extending horizontally for approximately three complete revolutions. The length of body 15, as measured along axis 22 from end 20 to end 21, may thus be approximately three times the length of pitch 23. A helical shape may have constant pitch, constant radius (measured in the plane perpendicular to the axis), constant torsion, constant curvature, constant ratio of curvature to torsion, and/or a straight axis. In FIG. 1, the radius of body 15 may be half of diameter 24. It is noted that the shape of body 15 resembles the general shape of deoxyribonucleic acid (DNA).

By way of non-limiting example, additional structures and/or features of body 15 may be described in U.S. Pat. No. 8,653,925, entitled "Double Helix Conductor," which issued Feb. 18, 2014, which is hereby incorporated into this disclosure by reference in its entirety. This patent may also be referred to as "the '925 patent" herein.

In FIG. 1, the shape of cross-section of runner 16 and runner 17 may be a rectangle that is approximately three times wider than it is tall. Furthermore, the width of runner 16 or runner 17 may be approximately $\frac{1}{13}^{th}$ of the pitch of said runner of body 15. As a result, runner 17 of body 15 resembles a ribbon having an inner surface 25 (facing axis 22 of the helical shape) and an outer surface 26 (facing the opposite way as inner surface 25). Runner 16 of body 15 resembles a ribbon having an inner surface 27 (facing axis 22 of the helical shape) and an outer surface 28 (facing the opposite way as inner surface 27). Note that embodiments of this disclosure are not intended to be limited by any of the given examples.

Runner 16, runner 17 and/or struts 18 may be manufactured from one or more of plastic, plastic plated with metals including copper, nickel, iron, soft iron, nickel alloys, and/or other metals and alloys, and/or other materials. In some embodiments, runner 16, runner 17 and struts 18 are manufactured from non-conductive material. Runner 16, runner 17, and/or struts 18 may be manufactured from different materials. Runner 16, runner 17, and/or struts 18 may be manufactured through integral construction or formed separately prior to being assembled. In some embodiments, runner 16, runner 17, and/or struts 18 may be include magnetically permeable material. In some embodiments, runner 16, runner 17, and/or struts 18 may be include non-ferromagnetic yet conducting material.

Figure 2:
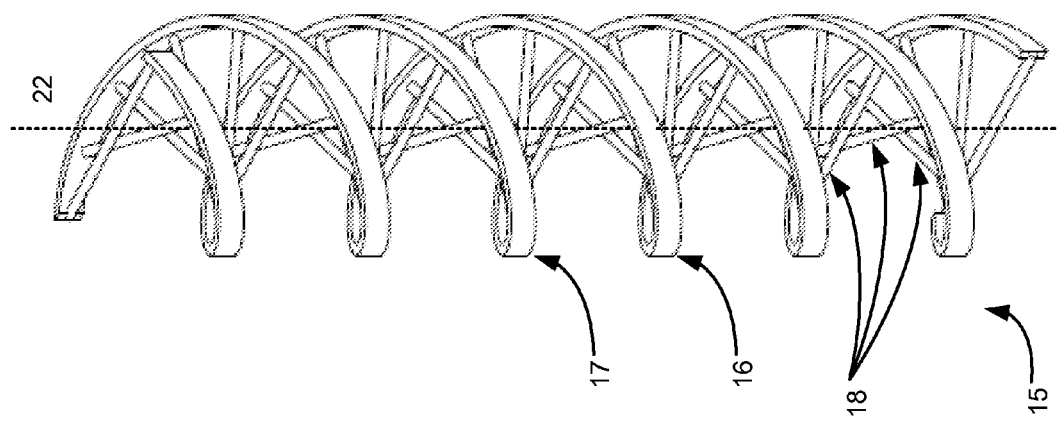
FIG. 2 illustrates an isometric view of an exemplary body including two intertwined helically wound runners, coupled by struts.

FIG. 2 illustrates an isometric view of an exemplary body 15 including two intertwined helically wound runners—runner 16 and runner 17—coupled by struts 18. Body 15 is shown here with axis 22 of both helically wound runners extending vertically.

Figure 3:
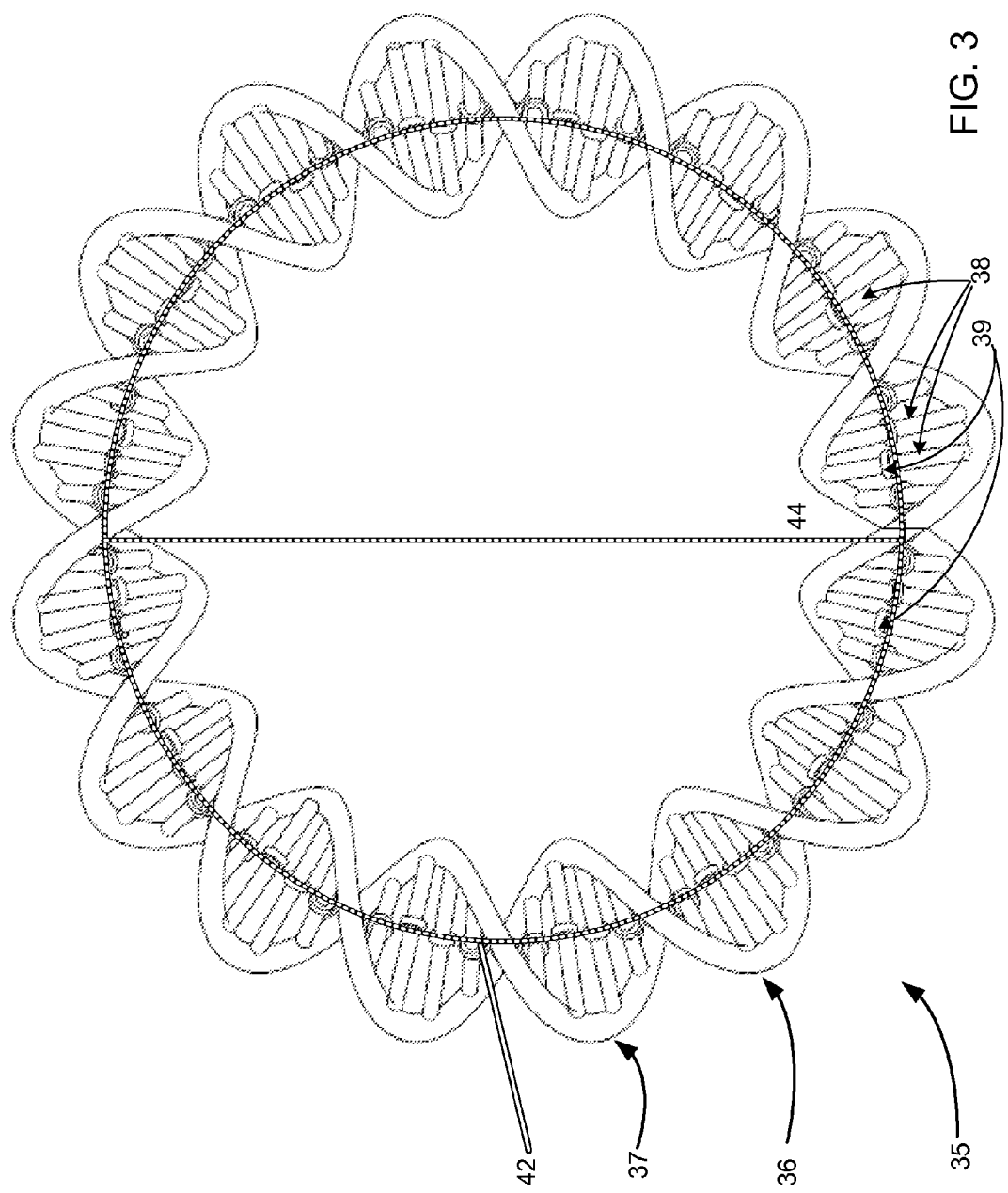
FIG. 3 illustrates a top-down view of an exemplary body including two intertwined helically wound runners sharing the same circular axis, both runners coupled by struts.

FIG. 3 illustrates a top-down view of an exemplary body 35 including two intertwined helically wound runners—runner 36 and runner 37—sharing the same circular axis 42, both runners coupled by struts 38. The resulting shape of body 35 may be referred to as toroidal. Body 35 may be formed the same as or similar to body 15, though comprising more revolutions, by arranging the body in a planar circular shape and joining both ends—end 20 and end 21 in FIG. 1—together. The preceding statement is not intended to limit the (process of) manufacture of bodies similar to or substantially the same as body 35 in any way.

Referring to FIG. 3, the diameter 44 of the circular axis of body 35, as well as the number of complete revolutions per runner required to completely extend along the entire circular axis 42 may be characteristic measurements/features of body 35. For example, as shown in FIG. 3, runner 36 and runner 37 of body 35 may require approximately eight complete revolutions around circular axis 42 to completely extend along the entire circular axis 42 of body 35, or some other number of rotations.

Note that one or more struts 38 of body 35 in FIG. 3 include a center-strut element 39, which is lacking from struts 18 of body 15. Center-strut element 39 may be associated with a particular strut of body 35.

Figure 4:
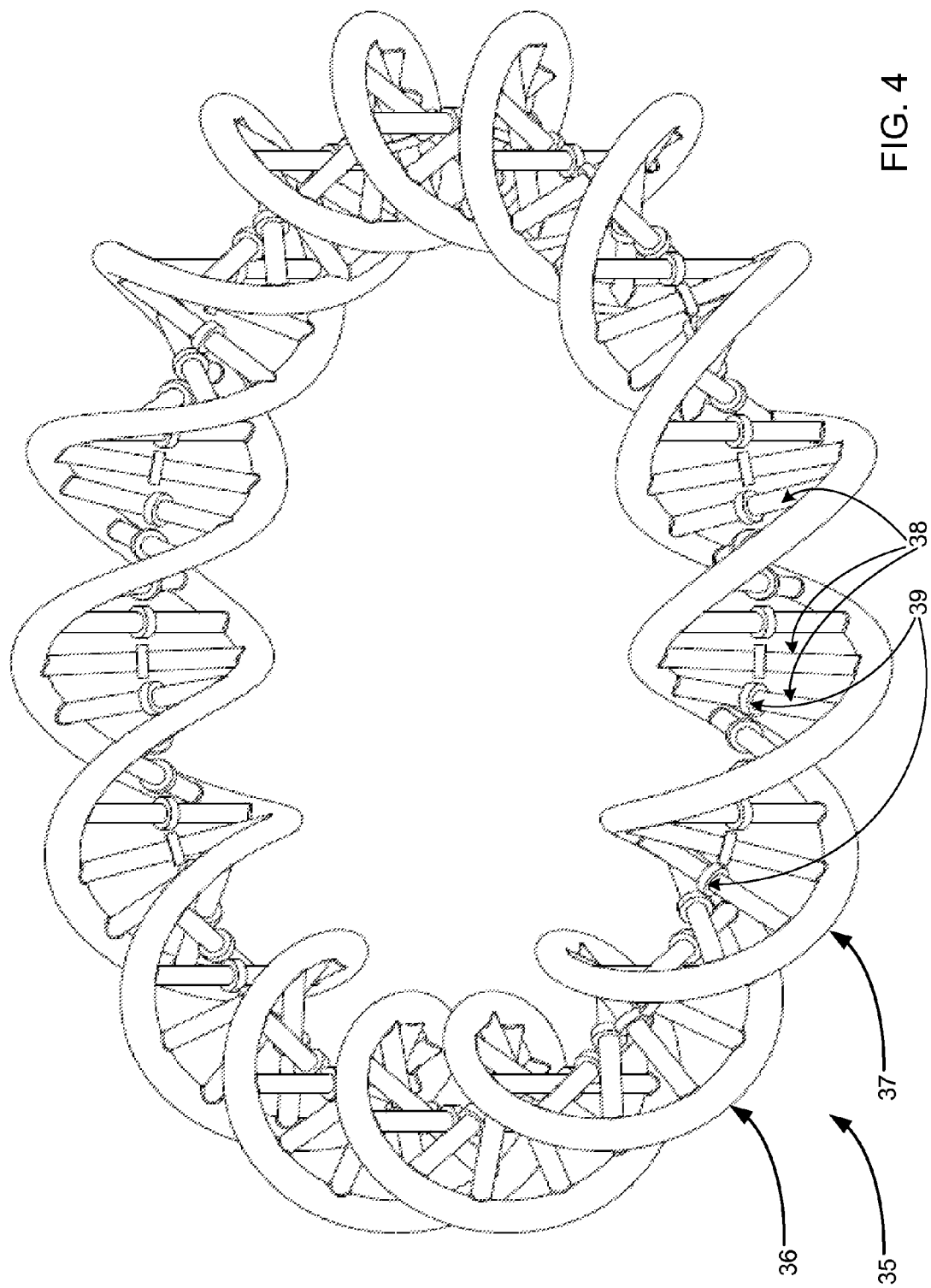
FIG. 4 illustrates an isometric view of an exemplary body including two intertwined helically wound runners sharing the same circular axis, both runners coupled by struts.

FIG. 4 illustrates an isometric view of an exemplary body 35 including two intertwined helically wound runners—runner 36 and runner 37—sharing the same circular axis, both runners coupled by struts 38. Note that, as in FIG. 3, the struts of body 35 in FIG. 4 may include a center-strut element 39, which may be lacking from struts 18 of body 15.

Figure 5:
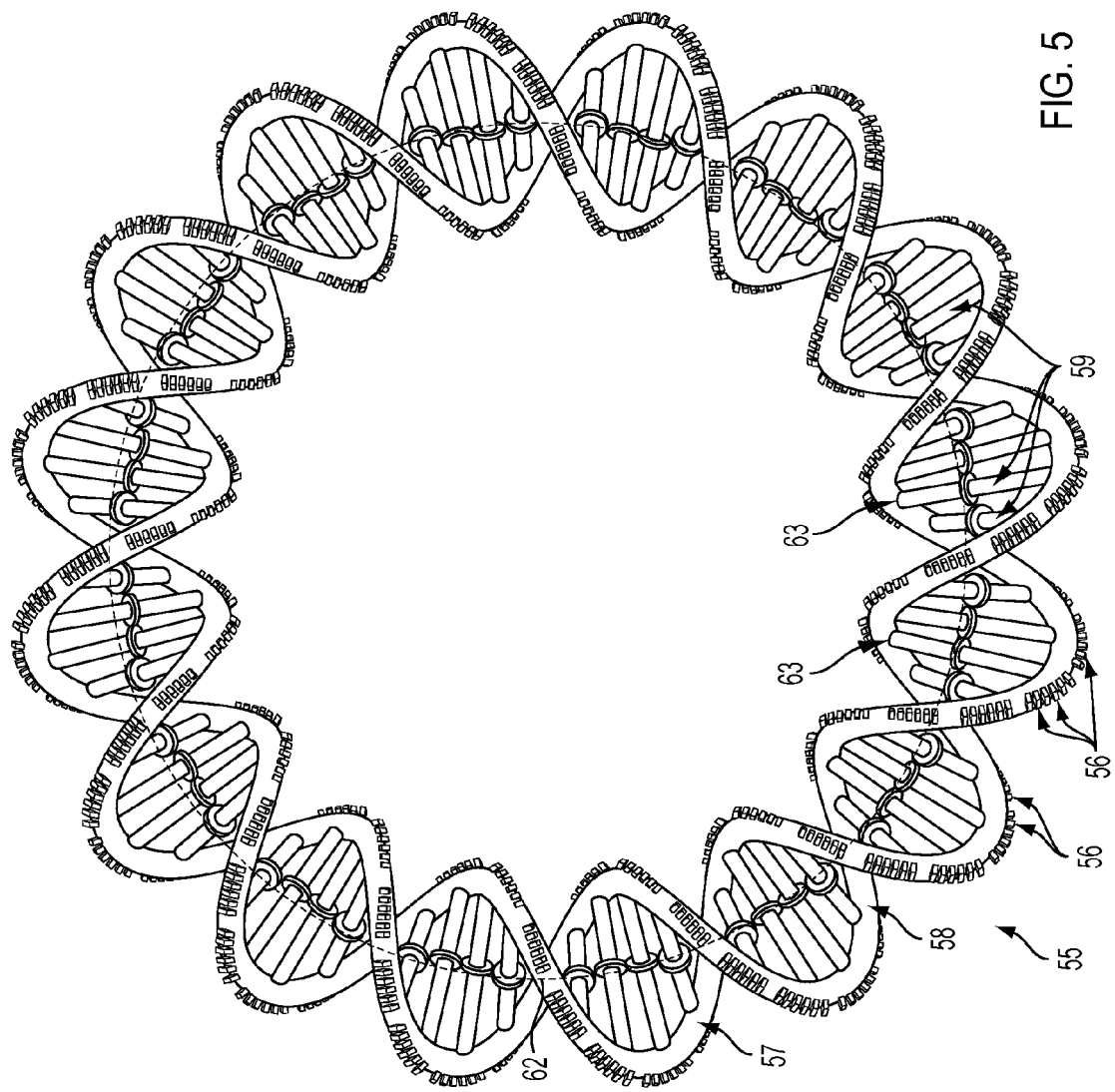
FIG. 5 illustrates a top-down view of an exemplary body including two intertwined helically wound runners sharing the same circular axis and having wire guides, both runners coupled by struts.

FIG. 5 illustrates a top-down view of an exemplary body 55 including two intertwined helically wound runners—runner 57 and runner 58—sharing the same circular axis 62 and having wire guides 56, both runners coupled by struts 59. Any part of runner 57 or runner 58 may include wire guides 56. Wire guides 56 may include grooves, notches, protrusions, slots, and/or other structural elements disposed on and/or in runner 57 or runner 58 and configured to guide a wire along at least a part of the surface of runner 57 or runner 58.

Such a wire, as any wire listed in any figure included in this description, may be insulated, uninsulated, or partially insulated and partially uninsulated. As used herein, a "wire" may include a set of twisted wires (which may interchangeably be referred to as a "twisted wire"), including but not limited to a set of two twisted wires. The number of turns of a set of twisted wires per inch and/or per helical revolution of a runner may be characteristic measurements/features of the system. In some embodiments, the number of twists per inch of a twisted wire may be about 2, about 5, about 10, about 20, about 100, and/or another suitable number of twists. In some embodiments, the frequency characteristics of an alternating current and/or the corresponding generated electromagnetic field may be based on, proportional to, and/or otherwise related to the number of twists of a twisted wire. For example, a higher number of twists per inch may correspond to a higher operating frequency for the alternating current and/or the corresponding generated electromagnetic field. In some embodiments, multiple twisted wires (e.g. a first twisted wire wound around a first runner and a second twisted wire wound around a second runner) may have the same direction of twisting, and/or a different direction of twisting. In some embodiments, multiple wires (e.g. twisted wires) may be wound around the same runner. In some embodiments, a wire may be wound around some or all of one or more struts.

Figure 6:
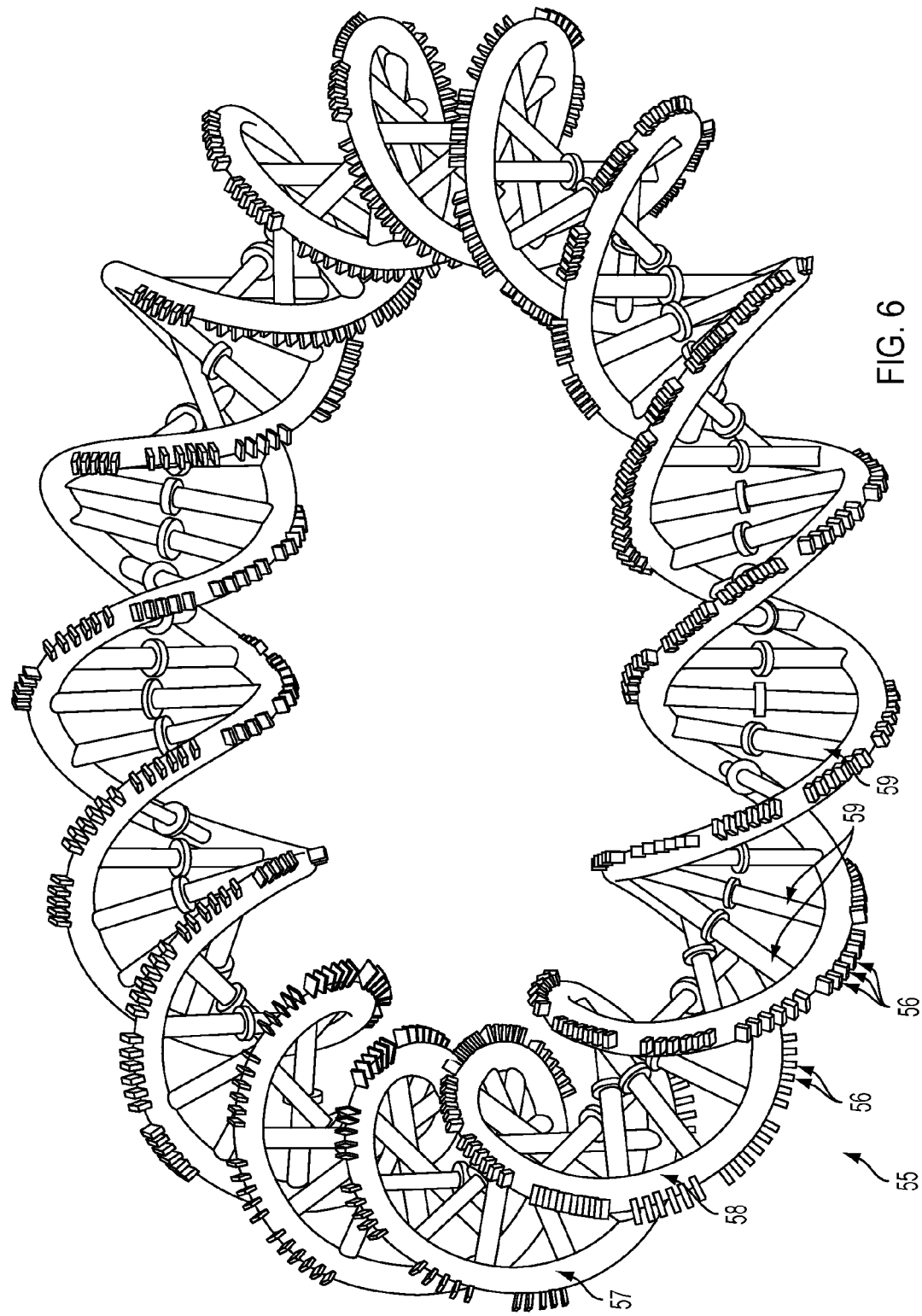
FIG. 6 illustrates an isometric view of an exemplary body including two intertwined helically wound runners sharing the same circular axis and having wire guides, both runner coupled by struts.

FIG. 6 illustrates an isometric view of an exemplary body 55 including two intertwined helically wound runners—runner 57 and runner 58—sharing the same circular axis and having wire guides 56, both runners coupled by struts 59.

Figure 7:
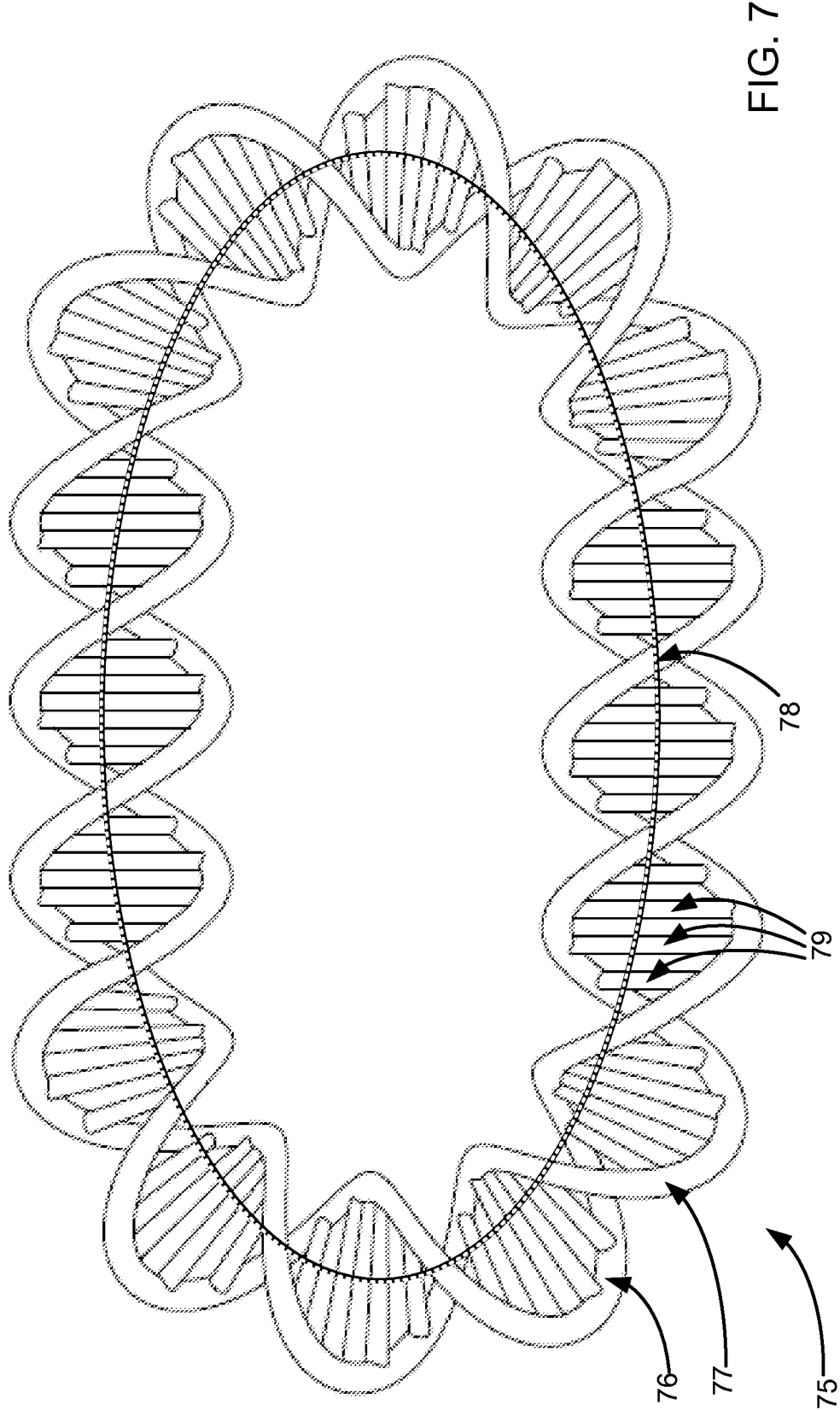
FIG. 7 illustrates an exemplary body including two intertwined helically wound runners sharing the same elliptical axis, both runner coupled by struts.

FIG. 7 illustrates an exemplary body 75 including two intertwined helically wound runners—runner 76 and runner 77—sharing the same elliptical axis 78, both runner coupled by struts 79. A body including two (or more) intertwined helically wound runners sharing the same axis may be arranged in any planar shape, including a circle, an oval, a triangle, a square, a rectangle, an angular shape, a polygon, and/or other planar shapes. Alternatively, and/or simultaneously, such a body may be arranged in a three-dimensional curve (a.k.a. space curve). In FIG. 7, body 75 may be formed from a body similar to body 15, though comprising more revolutions, by arranging the body in a planar elliptical shape and joining both ends—end 20 and end 21 in FIG. 1—together. The preceding statement is not intended to limit the (process of) manufacture of bodies similar to or substantially the same as body 75 in any way.

Figure 8:
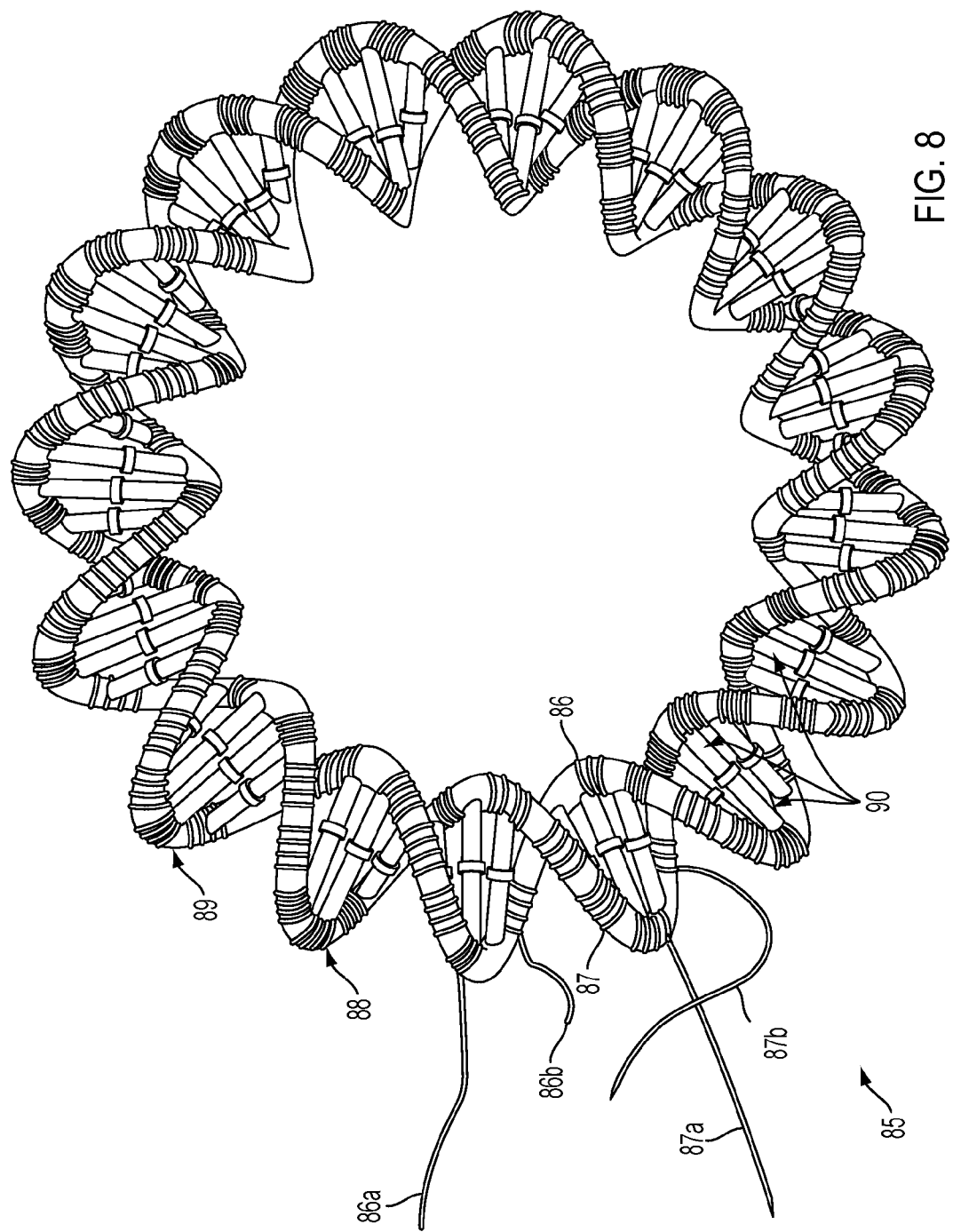
FIG. 8 illustrates a top-down view of an exemplary body including two intertwined helically wound runners sharing the same circular axis, both runners coupled by struts and having conductive wires spirally wound therearound.

FIG. 8 illustrates a top-down view of an exemplary body 85 including two intertwined helically wound runners—runner 88 and runner 89—sharing the same circular axis, coupled by struts 90 and having conductive wires—wire 86 and wire 87—spirally wound therearound. Wire 86 and/or wire 87, as any wire listed in any figure included in this description, may be insulated, uninsulated, or partially insulated and partially uninsulated. Wire 86 and/or wire 87, as any wire listed in any figure included in this description, may be a twisted wire. Runner 88 and runner 89 of body 85 may form cores around which wire 86 and wire 87 are spirally wound, respectively. As such, wire 86 and wire 87 may be arranged in a helical shape having axes that coincide with runner 88 and runner 89, respectively.

Wire 86 may include two leads—lead 86*a* and lead 86*b*. Wire 87 may include two leads—lead 87*a* and lead 87*b*. Wire 86 and wire 87 may be conductive. One or more bodies similar to or the same as body 85 may be used in an electrical system having one or more power sources and/or current sources arranged such that electrical coupling with one or both of wire 86 and wire 87 may be established, e.g. through coupling with lead 86*a* and 86*b* of wire 86 and through coupling with lead 87*a* and 87*b* of wire 87. The current supplied to wire 86 may be a direct current or an alternating current. The current supplied to wire 87 may be a direct current or an alternating current. The currents supplied to wire 86 and wire 87 may flow in the same direction or the opposite direction. For alternating currents, operating frequencies ranging from 0 Hz to 40 GHz are contemplated. The operating frequencies for wire 86 and wire 87 may be the same or different. Other electrical operating characteristics of current supplied to wire 86 and wire 87, such as phase, amplitude, power-level, and/or other operating characteristics, may be the same or different. The electrical system may be used to exploit the electromagnetic field that is created when electrical power is supplied to one or more wires of one or more bodies similar to or the same as body 85.

Figure 9:
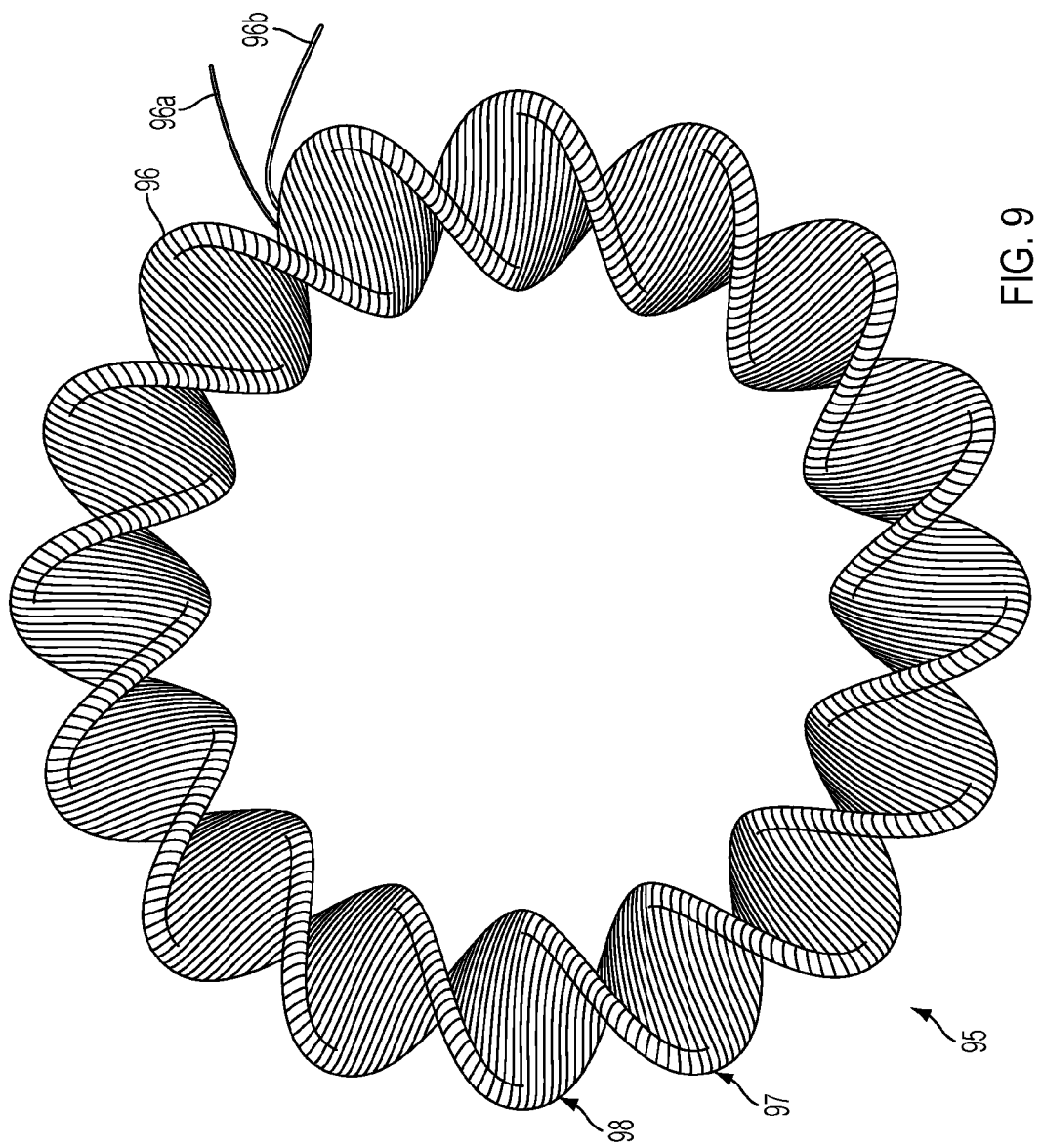
FIG. 9 illustrates a top-down view of an exemplary body including two intertwined helically wound runners sharing the same circular axis, both runner coupled by struts and having a wire spirally wound around both runners of the body.

FIG. 9 illustrates a top-down view of an exemplary body 95 including two intertwined helically wound runners—runner 97 and runner 98—sharing the same circular axis, both runner coupled by struts and having a wire 96 spirally wound around both runners of body 95. Wire 96 may include two leads—lead 86*a* and lead 86*b*. The resulting shape of body 95 with wire 96 may be referred to as a helicoidal shape. One or more bodies similar to or the same as body 95 may be used in an electrical system having a power source and/or a current source arranged such that electrical coupling with wire 96, e.g. through leads 96*a* and 96*b*, may be established. The electrical power supplied to wire 96 may include a direct current or an alternating current. Operating frequencies for an alternating current flowing through wire 96 are contemplated to range from 0 Hz to 40 GHz. The electrical system may be used to exploit the electromagnetic field that is created when electrical power is supplied.

Any of the bodies shown in FIGS. 1-9 may be used in an electrical system. Conductive wires may be spirally wound around one or more runners, one or more struts, and/or any combination thereof to produce electrical systems having specific electromagnetic properties when electrical power is supplied to one or more of the conductive wires.

Applications for any of the electrical systems described herein may include affecting growth and/or growth rate of plants and/or other organisms, medical applications, therapeutic applications, regenerative medicine, health applications, agriculture, treatment of humans and animals, material science, energy production, energy conversion, energy transformation, adenosine triphosphate (ATP) production, ATP transfer, ATP processing, and/or other applications.

In some embodiments, an electrical system including any of the bodies shown in FIGS. 1-9 (and/or multiple instances thereof) may be used as a component in an electrical circuit, performing one or more functions and/or applications including a (tunable) inductor, a (Tesla) coil, a transformer, a transducer, a transistor, a resistor, a solenoid, a stator for an electrical motor, an electromagnet, an electromagnetic pulse generator, an electromagnetic actuator, an energy conversion device, a position servomechanism, a generator, a stepping motor, a DC motor, a (contact-free) linear drive, an axial flux device, a measurement device for magnetic permeability, a dipole magnet, and a device to alter electron and/or particle trajectory.

Figure 10:
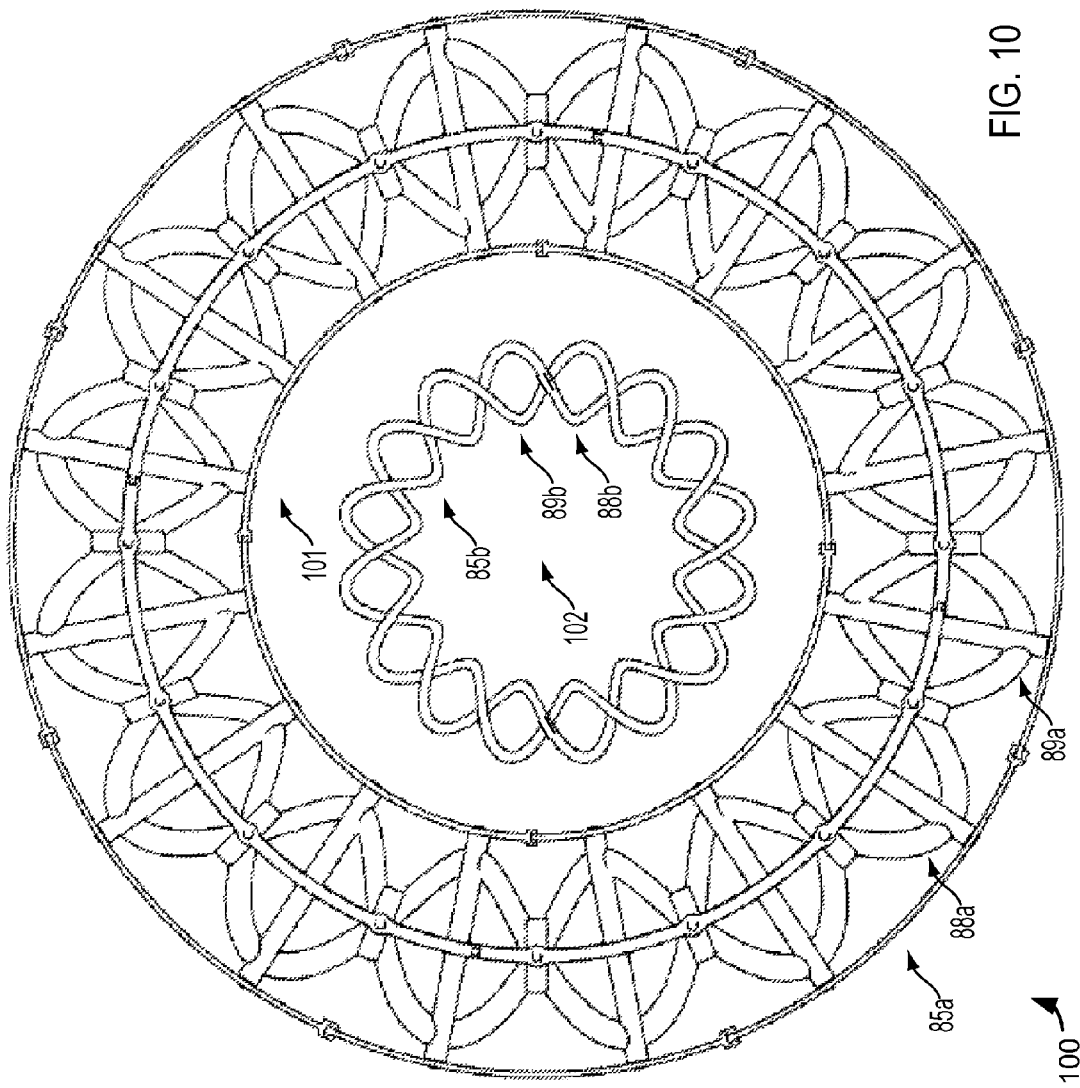
FIG. 10 illustrates a top-down view of an exemplary combination of two bodies arranged concentrically.

By way of illustration, FIG. 10 illustrates an electrical system 100 including two bodies similar to body 85 (shown in FIG. 8), depicted as a first body 85*a* and a second body 85*b*. Body 85*a* and body 85*b* may be the same as or similar to body 85 (shown in FIG. 8) and described herein. Body 85*a* may include a first runner 88*a* and a second runner 89*a*, which may be similar to or the same as runner 88 and runner 89 shown in FIG. 8. Body 85*b* may include a first runner 88*b* and a second runner 89*b*, which may be similar to or the same as runner 88 and runner 89 shown in FIG. 8. First body 85*a* may be arranged in a toroidal shape having a first centroid 101. Second body 85*b* may be arranged in a toroidal shape having a second centroid 102. Second body 85*b* may be arranged in a toroidal shape within first centroid 101. In some embodiments, second body 85*b* may be nested within first body 85*a*.

Referring to FIG. 10, in some embodiments, first body 85*a* and second body 85*b* may be arranged such that the toroidal shape of first body 85 and the toroidal shape of second body 85*b* are concentric. The toroidal shape of first body 85*a* may be planar and/or two-dimensional. The toroidal shape of second body 85*b* may be planar and/or two-dimensional. The toroidal shape of first body 85 may be arranged to be in the same plane as the toroidal shape of second body 85*b*. In some embodiments, the toroidal shape of first body 85 and the toroidal shape of second body 85*b* may be in parallel planes. Conductive wires may be wound around the runners depicted in FIG. 10.

Figure 11:
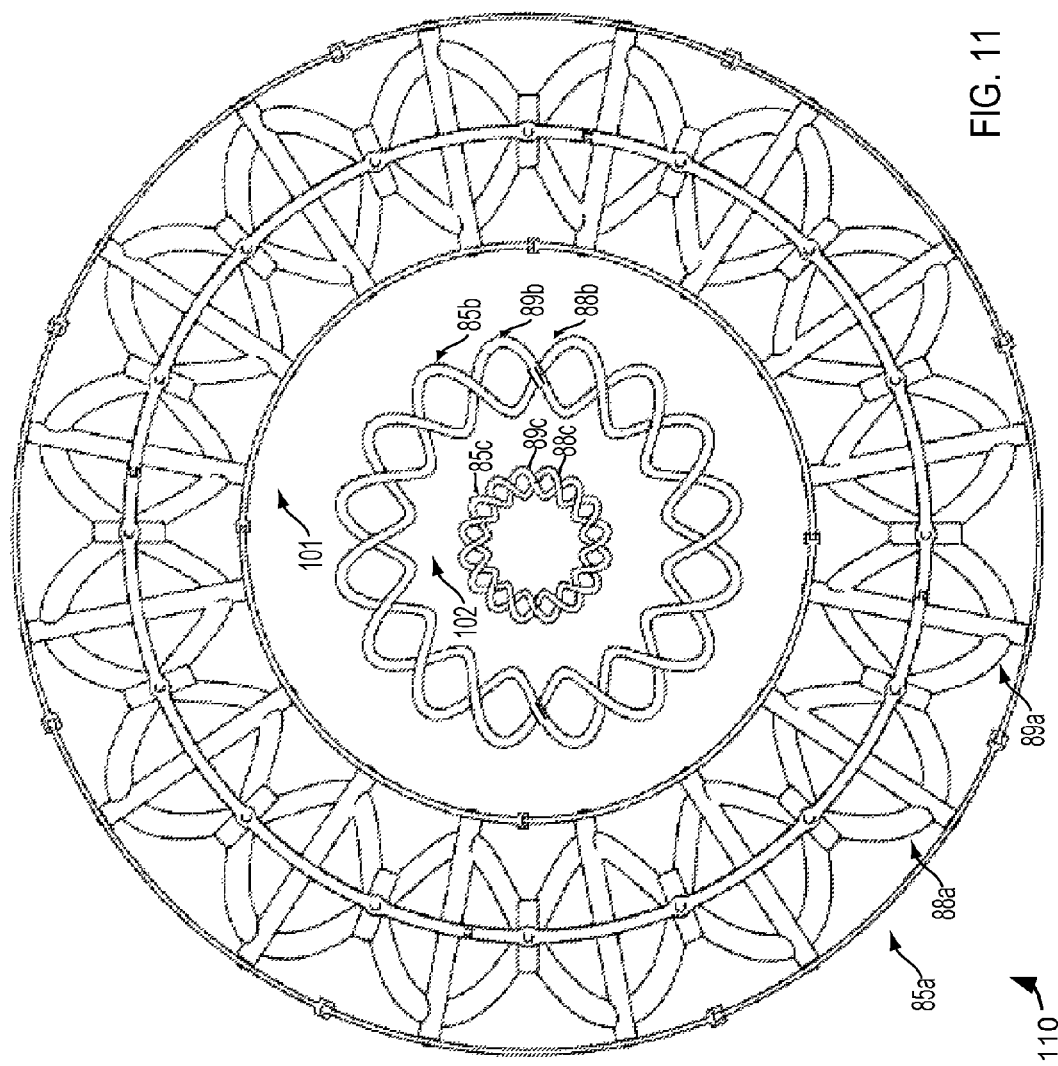
FIG. 11 illustrates a top-down view of an exemplary combination of three bodies arranged concentrically.

By way of illustration, FIG. 11 illustrates an electrical system 110 including three bodies similar to body 85 (shown in FIG. 8), depicted as first body 85*a*, second body 85*b*, and a third body 85*c*. Body 85*a*, body 85*b*, and body 85*c* may be the same as or similar to body 85 (shown in FIG. 8) and described herein. Body 85*c* may include a first runner 88*c* and a second runner 89*c*, which may be similar to or the same as runner 88 and runner 89 shown in FIG. 8. Third body 85*b* may be arranged in a toroidal shape within second centroid 102. In some embodiments, third body 85*c* may be nested within second body 85*b*.

Referring to FIG. 11, in some embodiments, first body 85*a*, second body 85*b*, and/or third body 85*c* may be arranged such that their respective toroidal shapes are concentric. The respective toroidal shapes may be planar and/or two-dimensional. The respective toroidal shapes may be arranged to be in the same plane. In some embodiments, the respective toroidal shapes may be in parallel planes. Conductive wires may be wound around the runners depicted in FIG. 11.

Figure 12:
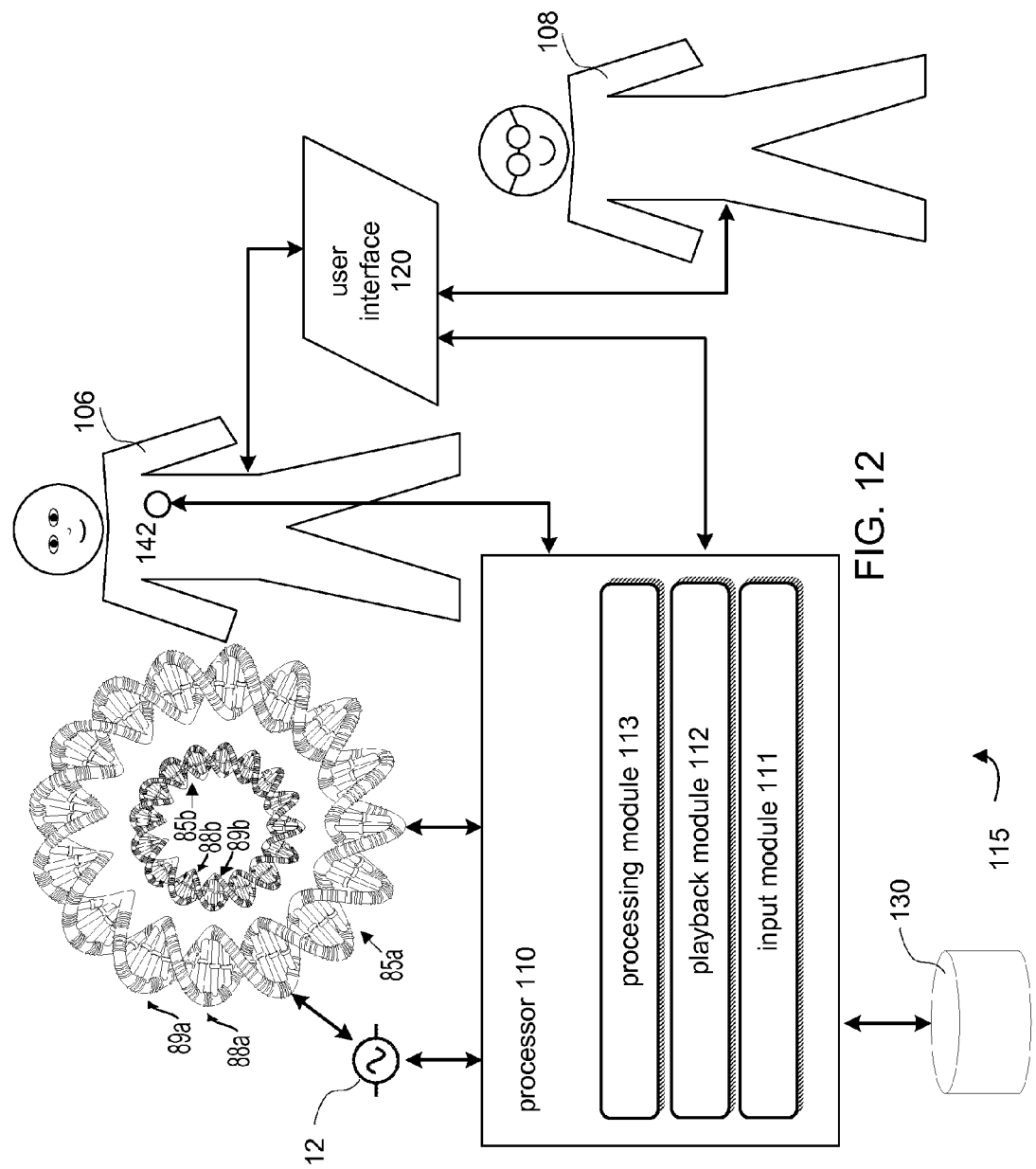
FIG. 12 schematically illustrates a system for providing therapy to a subject, according to one or more embodiments.

FIG. 12 schematically illustrates an electrical system 115 including two bodies similar to body 85 (shown in FIG. 8), indicates as first body 85*a* and second body 85*b* (similar to or the same as shown in FIG. 10). Electrical system 115 may further include one or more of a user interface 120, one or more physical processors 110, one or more sensors 142, electronic storage 130, one or more current sources 12, an input component 111, a playback component 112, a processing component 113, and/or other components.

Sensor(s) 142 may be configured to generate output signals conveying information. The information may include electrophysiological information and/or other information. In some embodiments, the one or more sensors 142 may include one or more of an audio sensor, a microphone, a stethoscope, a pressure sensor, a motion sensor, a proximity sensor, an electromagnetic sensor, an electrode, a temperature sensor, a current sensor, an optical sensor, an electro-optical sensor, and/or other sensors or combinations thereof. In some embodiments, the one or more processors 110 may be configured to provide information-processing capabilities and/or execute computer program components, including but not limited to input component 111, playback component 112, processing component 113, and/or other components. By way of non-limiting example, additional structures and/or features of sensor 142, processor 110, user interface 120, electronic storage 130, input component 111, playback component 112, and/or processing component 113, may be described in U.S. patent application Ser. No. 14/194,412, entitled "Health Applications for Using Bio-Feedback to Control an Electromagnetic Field," which was filed Feb. 28, 2014, which is hereby incorporated into this disclosure by reference in its entirety. This application may also be referred to as "the '412 application" herein.

The one or more current sources 12 may be configured to induce one or more currents across electrical leads, including but not limited to the electrical leads of the one or more conductive wires wound around the runners of first body 85a and/or second body 85b. In some embodiments, the one or more currents may include one or more alternating currents. In some embodiments, one or more induced currents may correspond to one or more sensor-generated output signals. In some embodiments, the one or more induced currents may correspond to one or more signals generated by a transducer and/or one or more other components of system 115.

Referring to FIG. 12, in some embodiments, the current supplied to the conductive wires wound around runners 88a and 89a of first body 85a may be the same or similar with regard to one or more electrical characteristics, including but not limited to frequency, amplitude, power level, and/or other electrical operating characteristics. In some embodiments, one or more electrical characteristics of the currents supplied to the conductive wires wound around runners 88a and 89a of first body 85a may be different. Alternatively, and/or simultaneously, the current supplied to the conductive wires wound around runners 88b and 89b of second body 85b may be the same or similar with regard to one or more electrical characteristics, including but not limited to frequency, amplitude, power level, and/or other electrical operating characteristics. In some embodiments, one or more electrical characteristics of the currents supplied to the conductive wires wound around runners 88b and 89b of second body 85b may be different.

In some embodiments, one or more electrical operating characteristics of the currents supplied to first body 85a may be the same as or similar to the currents supplied to second body 85b. For example, both bodies may be supplied with a 100 Hz alternating current. In some embodiments, one or more electrical operating characteristics of the currents supplied to first body 85a may be different than the currents supplied to second body 85b. For example, the frequency of the alternating current supplied to first body 85a (which may be referred to as the first frequency) may be different than the frequency of the alternating current supplied to second body 85b (which may be referred to as the second frequency). For example, the current supplied to first body 85a may be 1 A, whereas the current supplied to second body 85b may be 2 A or 3 A. For example, the current supplied to second body 85b may be 1 A, whereas the current supplied to first body 85a may be 2 A or 3 A. Other factors and/or ratios are considered within the scope of this disclosure.

In some embodiments, an alternating current supplied to first body 85a may be referred to as a first current, and an alternating current supplied to second body 85b may be referred to as a second current. In some embodiments, the first current and/or the second current may include a carrier signal and a modulating signal. In some embodiments, the carrier signal used for the first current and the second current may be similar or the same, e.g. having the same frequency. In some embodiments, carrier signals used for the first current and/or the second current may be radio-frequency signals. As used herein, radio frequency may refer to frequencies between about 30 kHz and about 30 GHz. In some embodiments, the modulating signal for the first current and/or the second current may be modulated through one or more of amplitude modulation, frequency modulation, phase modulation, digital modulation, and/or other types of modulation. In some embodiments, the modulating signal for the first current may include a first frequency. The modulating signal for the second current may include a second frequency.

In some embodiments, the first frequency and the second frequency may form an interval, e.g. a musical and/or harmonious interval. The interval may be defined by a specific type of musical tuning, including but not limited to twelve-tone equal temperament musical tuning. The first frequency and the second frequency may form a ratio, for example a small-integer ratio in which the ratio may be reducible to N/M, with both N and M being integers less than 50.

In some embodiments, the first frequency and the second frequency may be based on audio recordings of a note, tone, or chord, generated by a frequency generator and/or a (musical) instrument. For example, a first frequency may be based on the sound of a piano playing an A above middle C (also referred to as A4, which may include sound having a frequency of about 432 Hz, depending on the tuning system used). For example, a second frequency may be based on the sound of some instrument (e.g. a piano) playing a note forming a harmonious interval with A4, e.g. E5, which may include sound having a frequency of about 648 Hz. This tuning may be referred to as Pythagorean tuning. Mathematically perfect tuning may combine notes having a 3:2 ratio. Different types of tuning (or tuning systems), including but not limited to equal tempered tuning, may be used and considered within the scope of this disclosure.

Is some embodiments, an electrical system may include three bodies, as depicted in FIG. 11. The alternating currents supplied to the three bodies may be based on sounds having different frequencies, e.g. a first, second, and third frequency. These three frequencies may form intervals, e.g. musical and/or harmonious intervals, including but not limited to chords. For example, the first frequency may be 880 Hz (A5), the second frequency may be about 1046.50 (C6), and the third frequency may be about 1318.51 Hz (E6), thus forming an A-minor chord. In some embodiments, a set of harmonic intervals may be made using a different tuning. For example, an harmonic combination may be an 880 Hz note, a 1320 Hz note, and a 1660 Hz note.

Processor 110 may include one or more of a digital processor, an analog processor, a digital circuit designed to process information, a central processing unit, a graphics processing unit, an analog circuit designed to process information, and/or other mechanisms for electronically processing information. Although processor 110 is shown in FIG. 12 as a single entity, this is for illustrative purposes only. In some embodiments, processor 110 may include a plurality of processing units.

It should be appreciated that although components 111-113 are illustrated in FIG. 12 as being co-located within a single processing unit, in embodiments in which processor 110 includes multiple processing units, one or more of components 111-113 may be located remotely from the other components. The description of the functionality provided by the different components 111-113 described herein is for illustrative purposes, and is not intended to be limiting, as any of components 111-113 may provide more or less functionality than is described. For example, one or more of components 111-113 may be eliminated, and some or all of its functionality may be incorporated, shared, integrated into, and/or otherwise provided by other ones of components 111-113. Note that processor 110 may be configured to execute one or more additional components that may perform some or all of the functionality attributed below to one of components 111-113.

Input component 111 may be configured to obtain information, e.g. from one or more digital audio files, or, alternatively and/or simultaneously, based on sensor-generate output signals. In some embodiments, the information may be obtained from storage, e.g. from electronic storage. Information obtained from storage may include electronic audio files in any format, including but not limited to MP3, WMA, WAV, AIFF, and/or other audio formats. In some embodiments, information may be obtained from sound sources including frequency generators, phonographs, CD-players, DVD players, AM radio, FM radio, and/or other sound sources.

Processing component 113 may be configured to process the obtained information from input component 111. In some embodiments, processing component 113 may be configured to generate a processed signal based on the obtained information from input component 111. For example, processing module 113 may convert, filter, modify, and/or otherwise transform information or signals from input module 111 to generate the processed signal.

Playback component 112 may be configured to produce sound signals based on one or more of the obtained information from input component 111 and/or the processed signal from processing component 113. The sound signals produced by playback component 112 may be coupled electrically to the leads of one or more conductive wires wound around one or more runners of body 85a and/or body 85b such that the induced current corresponds to and/or is based on the sound signals. Alternatively, and/or simultaneously, the induced current may be controlled by and/or based on the sound signals produced by playback component 112. In some embodiments, the sound signals produced by playback module 112 may be amplified by an amplifier before being electrically coupled to the leads of one or more conductive wires. In some preferred embodiments, the amplifier may be an audio amplifier ranging between 100 W and 400 W. Other types of amplifiers and/or amplifiers having a different power range are also contemplated.

Figure 14A:
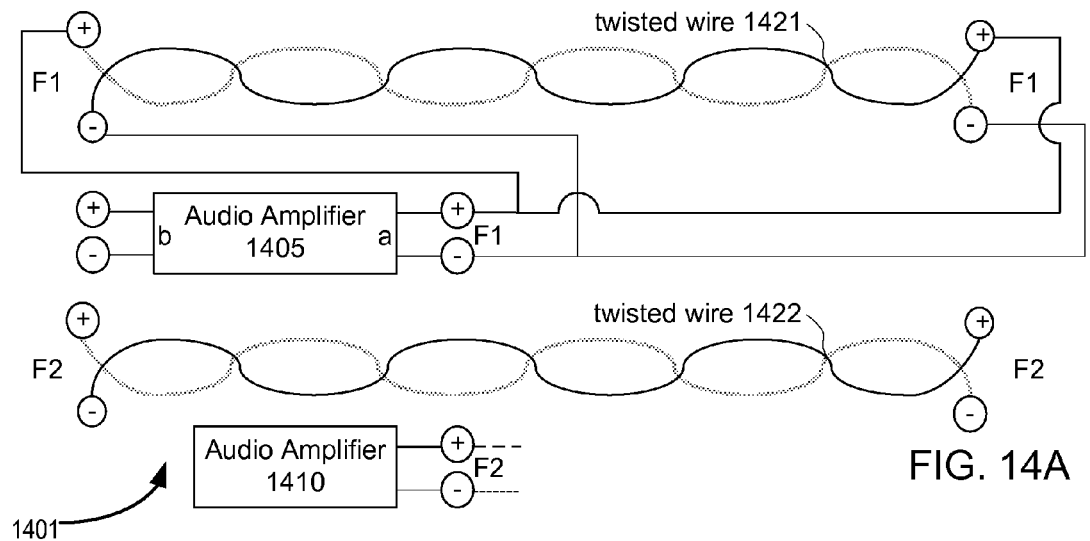
FIG. 14A-14B illustrate wiring diagrams for wiring wires around runners, according to one or more embodiments.

FIG. 14A illustrates a wiring diagram 1401 for wiring a twisted wire 1421 and/or a twisted wire 1422 around one or more runners of a body having two or more intertwined helically wound runners, as described elsewhere in this disclosure. In some embodiments, twisted wire 1421 may be wound around a first runner (e.g. the same as or similar to runner 88 shown in FIG. 8). One or more signals may be provided to twisted wire 1421 through four leads (indicated by a circled positive or negative sign in FIG. 14A). The signal provided to twisted wire 1421 may be based on audio recordings of a note, tone, or chord, generated by a frequency generator, a (musical) instrument, and/or another sound source. By way of non-limiting example, the signal may be similar to or based on the information obtained by an input component (e.g. the same as or similar to input component 111 shown in FIG. 12), the processed signal generated by a processing component (e.g. the same as or similar to processing component 113 shown in FIG. 2), a sound signal produced by a playback component (e.g. the same as or similar to playback component 112 shown in FIG. 12), and/or an amplified signal from an audio amplifier 1405. In some embodiments, audio amplifier 1405 may support multiple audio channels, e.g. a channel "a" and a channel "b" as illustrated by labels "a" and "b" in FIG. 14A. The signal on channel "a" of audio amplifier 1405 is labeled "F1." In some embodiments, signal F1 may substantially include and/or be based on a particular frequency. As shown in FIG. 14A, the positive side of signal F1 may be electrically and/or operationally connected to two of the four leads of twisted wire 1421, wherein the two selected leads are on opposite ends of twisted wire 1421. The negative side of signal F1 may be electrically and/or operationally connected to the remaining two of the four leads of twisted wire 1421, which may be on opposite ends of twisted wire 1421.

In some embodiments, wiring diagram 1401 may include a second twisted wire 1422. In some embodiments, twisted wire 1422 may be wound around a second runner (e.g. the same as or similar to runner 89 shown in FIG. 8). One or more signals may be provided to twisted wire 1422 through four leads (indicated by a circled positive or negative sign in FIG. 14A). The signal provided to twisted wire 1422 may, in some embodiments, be the same as the signals provided to twisted wire 1421, e.g. the F1 signal. In some embodiments, the signal provided to twisted wire 1422 may be provided by channel "b" of audio amplifier 1405. In some embodiments, the signal provided to twisted wire 1422 may be provided by one or more channels of an audio amplifier 1410. The signal of audio amplifier 1410 is labeled "F2." In some embodiments, signal F2 may substantially include and/or be based on a particular frequency, which may be a different frequency than the frequency used for signal F1. For example, signal F1 may be based on a frequency of 250 Hz, and signal F2 may be based on a frequency of four times the frequency of signal F1, e.g. 1000 Hz. Likewise, signals F1 and F2 may be 216 Hz and 864 Hz, respectively, by way of non-limiting example. As indicated in FIG. 14A, the positive side of signal F2 may be electrically and/or operationally connected the two positive leads of twisted wire 1422, on opposite ends of twisted wire 1422. The negative side of signal F1 may be electrically and/or operationally connected to the two negative leads of twisted wire 1422, on opposite ends of twisted wire 1422.

Figure 14B:
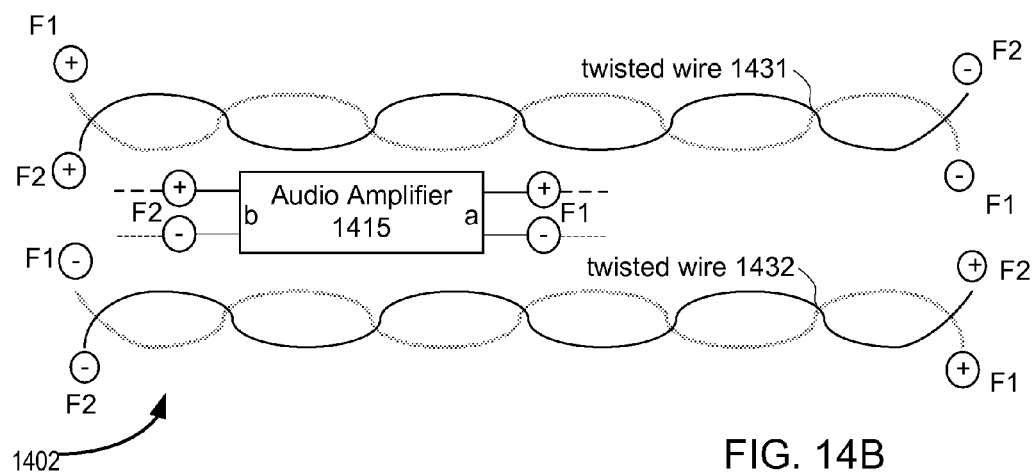

FIG. 14B illustrates a wiring diagram 1402 for wiring a twisted wire 1431 and a twisted wire 1432 around two runners of a body having two intertwined helically wound runners, as described elsewhere in this disclosure. In some embodiments, twisted wire 1431 may be wound around a first runner (e.g. the same as or similar to runner 88 shown in FIG. 8). In some embodiments, twisted wire 1432 may be wound around a second runner (e.g. the same as or similar to runner 89 shown in FIG. 8). One or more signals may be provided to twisted wire 1431 through four leads and to twisted wire 1432 through four leads (indicated by a circled positive or negative sign in FIG. 14B). In some embodiments, the signals provided to twisted wire 1431 and 1432 may be provided by an audio amplifier 1415 that supports multiple audio channels, e.g. a channel "a" and a channel "b" as illustrated by labels "a" and "b" in FIG. 14B. The signal on channel "a" of audio amplifier 1415 is labeled "F1." The signal on channel "b" of audio amplifier 1415 is labeled "F2." As shown in FIG. 14B, the positive side of signal F1 may be electrically and/or operationally connected to two of the eight leads of twisted wires 1431 and 1432, wherein the two selected leads are on opposite ends. The negative side of signal F1 may be electrically and/or operationally connected to two other leads of twisted wires 1431 and 1432, which may be on opposite ends of twisted wire 1421. As shown in FIG. 14B, the positive side of signal F2 may be electrically and/or operationally connected to two of the eight leads of twisted wires 1431 and 1432, wherein the two selected leads are on opposite ends. The negative side of signal F2 may be electrically and/or operationally connected to two other leads of twisted wires 1431 and 1432, which may be on opposite ends of twisted wire 1421. In some embodiments using wiring diagram 1402, signal F1 may be based on a frequency of 250 Hz, and signal F2 may be based on a frequency of four times the frequency of signal F1, e.g. 1000 Hz. Likewise, signals F1 and F2 may be 216 Hz and 864 Hz, respectively, by way of non-limiting example.

In some embodiments, the wiring of two twisted wires around two intertwined helically wound runners as shown in wiring diagram 1401 and/or wiring diagram 1402 may be used as a basis for wiring an electrical system having two, three, or more bodies arranged in each other's proximity. such an electrical system may be the same as or similar to system 100 shown in FIG. 10 or system 110 shown in FIG. 11. For example, in an electrical system using two bodies that each include two intertwined helically wound runners, the four runners may be wound with four twisted wires having a total of 16 leads that may be used to electrically and/or operationally connected to 1, 2, and/or 4 audio amplifiers and/or channels thereof that are the same as or similar to audio amplifier 1405, audio amplifier 1410, and/or audio amplifier 1415 (e.g. using channels "a" and "b").

Electronic storage 130 of system 115 in FIG. 12 comprises electronic storage media that electronically stores information. The electronic storage media of electronic storage 130 may include one or both of system storage that is provided integrally (i.e., substantially non-removable) with system 115 and/or removable storage that is connectable to system 115 via, for example, a port (e.g., a USB port, a Firewire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 115 to function properly. For example, electronic storage 130 may store sound information and/or electronic audio files (as discussed elsewhere herein), and/or other information. Electronic storage 130 may be a separate component within system 115, or electronic storage 130 may be provided integrally with one or more other components of system 115 (e.g., processor 110).

User interface 120 of system 115 in FIG. 12 is configured to provide an interface between system 115 and a user (e.g., a user 108, a subject 106, a caregiver, a therapy decision-maker, etc.) through which the user can provide information to and receive information from system 115. This enables data, results, and/or instructions and any other communicable items, collectively referred to as "information," to be communicated between the user and system 115. An example of information that may be conveyed to user 108 is an indication of the volume and/or intensity of the sound signals produced by playback module 112. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 115 from removable storage (e.g., a smart card, a flash drive, a removable disk, etc.) that enables the user(s) to customize system 115. Other exemplary input devices and techniques adapted for use with system 115 as user interface 120 include, but are not limited to, an RS-232 port, RF link, an IR link, modem (telephone, cable, Ethernet, internet or other). In short, any technique for communicating information with system 115 is contemplated as user interface 120.

Figure 13:
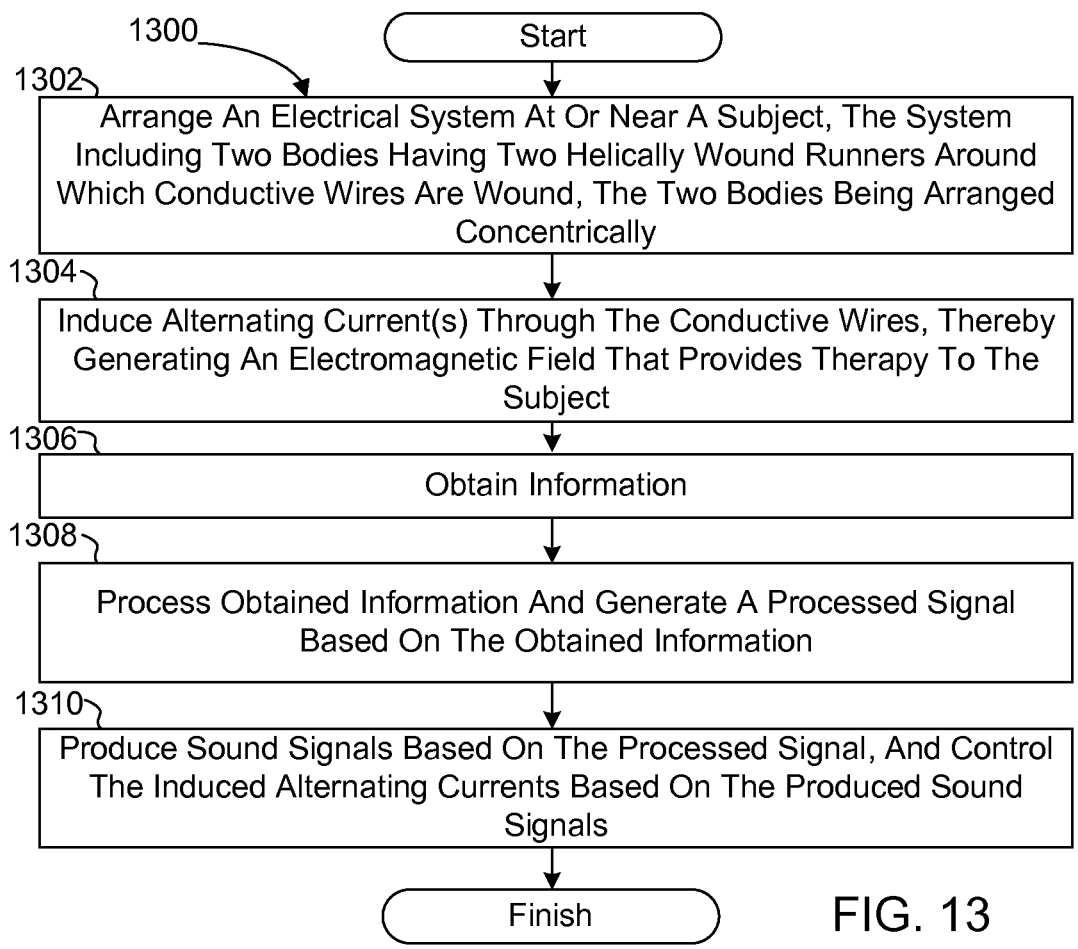
FIG. 13 illustrates a method for providing therapy to a subject, according to one or more embodiments.

FIG. 13 illustrates a method 1300 for providing therapy to a subject. The operations of method 1300 presented below are intended to be illustrative. In certain embodiments, method 1300 may be accomplished with one or more additional operations not described, and/or without one or more of the operations discussed. Additionally, the order in which the operations of method 1300 are illustrated in FIG. 13 and described below is not intended to be limiting.

In certain embodiments, method 1300 may be implemented in one or more processing devices (e.g., a digital processor, an analog processor, a digital circuit designed to process information, an analog circuit designed to process information, and/or other mechanisms for electronically processing information). The one or more processing devices may include one or more devices executing some or all of the operations of method 1300 in response to instructions stored electronically on an electronic storage medium. The one or more processing devices may include one or more devices configured through hardware, firmware, and/or software to be specifically designed for execution of one or more of the operations of method 1300.

Regarding method 1300, at an operation 1302, at an operation 1302, an electrical system is arranged at or near the subject. The electrical system includes a first body and a second body. The first body includes a first runner and a second runner. The first runner and the second runner are helically intertwined. The first body is arranged in a first toroidal shape having a first centroid. A first conductive wire is wound around the first runner and a second conductive wire is wound around the second runner. The second body includes a third runner and a fourth runner. The third runner and the fourth runner are helically intertwined. The second body is arranged in a second toroidal shape having a second centroid. A third conductive wire is wound around the third runner and a fourth conductive wire is wound around the fourth runner. The second body is arranged in a second toroidal shape within the first centroid. The first body and the second body are arranged such that the first toroidal shape and the second toroidal shape are concentric. In some embodiments, operation 1302 is performed by an electrical system the same as or similar to electrical system 115 (shown in FIG. 12 and described herein).

At an operation 1304, one or more alternating currents are induced through the first conductive wire, the second conductive wire, the third conductive wire, and the fourth conductive wire such that the one or more alternating currents create an electromagnetic field at or near at least one of the first centroid and the second centroid. The electromagnetic field provides therapy to a subject. In some embodiments, operation 1304 is performed by one or more current sources the same as or similar to current source 12 (shown in FIG. 12 and described herein).

At an operation 1306, information is obtained by a physical processor. In some embodiments, operation 1306 is performed by a processor and/or computer program component the same as or similar to processor 110 and/or input component 111 (shown in FIG. 12 and described herein).

At an operation 1308, the obtained information is processed and a processed signal is generated based on the obtained information. In some embodiments, operation 1308 is performed by a processing component the same as or similar to processing component 113 (shown in FIG. 12 and described herein).

At an operation 1310, sound signals are produced based on the processed signal. The induced one or more alternating currents are based on the produced sound signals. In some embodiments, operation 1310 is performed by a playback component the same as or similar to playback component 112 (shown in FIG. 12 and described herein).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An electrical system comprising:
 a first body including two runners, the runners being a first runner and a second runner, wherein the first runner and the second runner are intertwined helically wound runners, wherein the first body is arranged in a first toroidal shape having a first centroid;
 a first conductive wire spirally wound around the first runner;
 a second conductive wire spirally wound around the second runner;
 a second body including two runners, the runners being a third runner and a fourth runner, wherein the third runner and the fourth runner are intertwined helically wound runners, wherein the second body is arranged in a second toroidal shape within the first centroid;
 a third conductive wire spirally wound around the third runner;
 a fourth conductive wire spirally wound around the fourth runner,
 wherein the first body and the second body are arranged such that the first toroidal shape and the second toroidal shape are concentric; and
 one or more alternating current sources, wherein the one or more alternating current sources are arranged to electrically couple with the first conductive wire, the second conductive wire, the third conductive wire, and the fourth conductive wire to supply alternating current, wherein the one or more alternating current sources are configured to induce one or more alternating currents through the first conductive wire, the second conductive wire, the third conductive wire, and the fourth conductive wire such that the one or more alternating currents create an electromagnetic field at or near at least one of the first centroid and the second centroid.

2. The electrical system of claim 1, wherein the electrical system is configured to generate an electromagnetic field responsive to the one or more alternating currents being supplied, wherein the electromagnetic field provides therapy to a subject.

3. The electrical system of claim 1, wherein the one or more alternating current sources operate between 0 Hz and 40 GHz.

4. The electrical system of claim 1, wherein the one or more alternating current sources operate between about 20 Hz and about 20 kHz.

5. The electrical system of claim 1, wherein the first conductive wire is a twisted wire, wherein the second conductive wire is a twisted wire, wherein the third conductive wire is a twisted wire, and wherein the fourth conductive wire is a twisted wire.

6. The electrical system of claim 1, wherein the first conductive wire is spirally wound around the first runner such that the first conductive wire is arranged in a helical shape having an axis that coincides with the first runner.

7. The electrical system of claim 1, wherein the two runners included in the first body are arranged in between 2 and 10000 revolutions in the first body.

8. The electrical system of claim 1, wherein the first conductive wire is spirally wound such that the first conductive wire revolves around the first runner between 2 and 10000 times per revolution.

9. The electrical system of claim 1, wherein a planar shape of the first body is one of a circle, an oval, a triangle, a square, an angular shape, or a polygon.

10. The electrical system of claim 1, wherein the one or more alternating current sources include a first current source and a second current source, wherein the first current source supplies a first alternating current having a first frequency to the first conductive wire and second conductive wire, wherein the second current source supplies a second alternating current having a second frequency to the third conductive wire and fourth conductive wire.

11. The electrical system of claim 10, wherein the first current source operates at a power level that is the same as a second power level of the second current source.

12. The electrical system of claim 10, wherein the first current source operates at a first power level, wherein the second current source operates at a second power level, and wherein the first power level is a multiple of the second power level.

13. The electrical system of claim 10, wherein the first current source operates at a first power level, wherein the second current source operates at a second power level, and wherein the second power level is a multiple of the first power level.

14. The electrical system of claim 10, wherein the first frequency is the same as the second frequency.

15. The electrical system of claim 10, wherein the first frequency is different than the second frequency.

16. The electrical system of claim 10, wherein the first frequency is a multiple of the second frequency.

17. The electrical system of claim 10, wherein the second frequency is a multiple of the first frequency.

18. The electrical system of claim 10, wherein the first alternating current includes a first carrier signal and a first modulating signal, wherein the second alternating current includes a second carrier signal and a second modulating signal.

19. The electrical system of claim 18, wherein the first carrier signal has the same frequency as the second carrier signal.

20. The electrical system of claim 19, wherein the first carrier signal has a radio frequency.

21. The electrical system of claim 18, wherein the first carrier signal has a different frequency than the second carrier signal.

22. The electrical system of claim 18, wherein the first modulating signal is modulated through one or more of amplitude modulation, frequency modulation, and/or phase modulation.

23. The electrical system of claim 18, wherein the first modulating signal has a first signal frequency, wherein the second modulating signal has a second signal frequency.

24. The electrical system of claim 23, wherein the first signal frequency and the second signal frequency form a harmonious interval.

25. The electrical system of claim 23, wherein the first signal frequency and the second signal frequency form an interval having a small-integer ratio.

26. The electrical system of claim 23, wherein the first signal frequency and the second signal frequency form an interval of a musical tuning.

27. The electrical system of claim 23, wherein the first signal frequency and the second signal frequency form an interval in twelve-tone equal temperament tuning.

28. The electrical system of claim 23, wherein the first signal frequency is a multiple of the second signal frequency.

29. The electrical system of claim 1, wherein the second toroidal shape has a second centroid, the system further comprising:
a third body including two runners, the runners being a fifth runner and a sixth runner, wherein the fifth runner and the sixth runner are intertwined helically wound runners, wherein the third body is arranged in a third toroidal shape within the second centroid;
a fifth conductive wire spirally wound around the fifth runner; and
a sixth conductive wire spirally wound around the sixth runner,
wherein the first body, the second body, and the third body are arranged such that the first toroidal shape, the second toroidal shape, and the third toroidal shape are concentric.

30. The electrical system of claim 1, further comprising:
one or more physical processors configured via computer-readable instructions to:
obtain information;
process the obtained information and generate a processed signal based on the obtained information, and
produce sound signals based on the processed signal,
wherein the one or more alternating currents are based on the produced sound signals.

31. The electrical system of claim 30, wherein the obtained information includes one or more digital audio files.

32. The electrical system of claim 30, wherein the one or more alternating currents are dynamically controlled to correspond to the produced sound signals such that one or more frequencies of the one or more alternating currents correspond to one or more frequencies of the produced sound signals.

33. A method for providing therapy to a subject by using electromagnetic fields, the method comprising:
arranging an electrical system at or near the subject, wherein the electrical system includes a first body and a second body, wherein the first body includes a first runner and a second runner, wherein the first runner and the second runner are helically intertwined, wherein the first body is arranged in a first toroidal shape having a first centroid, wherein a first conductive wire is wound around the first runner and a second conductive wire is wound around the second runner, wherein the second body includes a third runner and a fourth runner, wherein the third runner and the fourth runner are helically intertwined, wherein the second body is arranged in a second toroidal shape having a second centroid, wherein a third conductive wire is wound around the third runner and a fourth conductive wire is wound around the fourth runner, wherein the second body is arranged in a second toroidal shape within the first centroid, wherein the first body and the second body are arranged such that the first toroidal shape and the second toroidal shape are concentric;
inducing alternating currents through the first conductive wire, the second conductive wire, the third conductive wire, and the fourth conductive wire such that the alternating currents create an electromagnetic field at or near at least one of the first centroid and the second centroid, wherein the electromagnetic field provides therapy to a subject;
obtaining, by a physical processor, information;
processing the obtained information and generating a processed signal based on the obtained information; and
producing sound signals based on the processed signal, wherein the alternating currents are based on the produced sound signals.

34. The method of claim 33, wherein the alternating currents are dynamically controlled to correspond to the produced sound signals such that one or more frequencies of the alternating currents correspond to one or more frequencies of the produced sound signals.

* * * * *